(12) United States Patent
Aebi et al.

(10) Patent No.: US 9,956,021 B1
(45) Date of Patent: May 1, 2018

(54) TENSIONING AND CRIMPING TOOL FOR ORTHOPEDIC CABLE TENSIONING

(71) Applicant: DEPUY SYNTHES PRODUCTS, INC., Raynham, MA (US)

(72) Inventors: This Aebi, Grenchen (CH); Simon M. Bosshard, Bern (CH); Rhett A. Rapier, Trimbach (CH)

(73) Assignee: Depuy Synthes Products, Inc., Raynham, MA (US)

( * ) Notice: Subject to any disclaimer, the term of this patent is extended or adjusted under 35 U.S.C. 154(b) by 0 days. days.

(21) Appl. No.: 15/397,579

(22) Filed: Jan. 3, 2017

(51) Int. Cl.
| A61B 17/58 | (2006.01) |
| A61B 17/88 | (2006.01) |
| A61B 17/00 | (2006.01) |
| A61B 90/00 | (2016.01) |

(52) U.S. Cl.
CPC ...... *A61B 17/8861* (2013.01); *A61B 17/8869* (2013.01); *A61B 2017/0046* (2013.01); *A61B 2017/00477* (2013.01); *A61B 2090/034* (2016.02); *A61B 2090/036* (2016.02); *A61B 2090/0807* (2016.02)

(58) Field of Classification Search
CPC ............ A61B 17/8861; A61B 17/8869; A61B 17/8872; A61B 2090/034
See application file for complete search history.

(56) References Cited

U.S. PATENT DOCUMENTS

| 4,387,631 | A | * | 6/1983 | Pasic | B65B 13/22 |
| | | | | | 100/32 |
| 4,417,735 | A | * | 11/1983 | Heisler | F16L 25/0018 |
| | | | | | 277/608 |
| 5,199,146 | A | * | 4/1993 | Grover | B25B 23/0092 |
| | | | | | 29/268 |
| 5,284,010 | A | * | 2/1994 | Dammann | B65H 54/71 |
| | | | | | 242/473.5 |
| 5,423,820 | A | * | 6/1995 | Miller | A61B 17/82 |
| | | | | | 24/129 W |
| 6,068,648 | A | | 5/2000 | Cole et al. | |
| 6,544,267 | B1 | | 4/2003 | Cole et al. | |
| 6,761,722 | B2 | | 7/2004 | Cole et al. | |
| 8,469,966 | B2 | | 6/2013 | Allen et al. | |

(Continued)

FOREIGN PATENT DOCUMENTS

WO    WO2013012433    1/2013

*Primary Examiner* — Ellen C Hammond
*Assistant Examiner* — Stuart S Bray
(74) *Attorney, Agent, or Firm* — Kramer Amado, P.C.

(57) ABSTRACT

Various embodiments relate to a tensioning and crimping tool, the tensioning and crimping tool including a housing unit, a crimping section including a housing, a trigger-handle mounted to the housing, a crimping unit, including an inner crimping tube and an outer crimping tube, where the outer crimping tube is mounted around the inner crimping tube and configured to move in an axial direction relative to the inner crimping tube to crimp a crimp onto the cable, a tensioning section including the housing, a collet opener end, and a tensioning unit including a collet, a cone sheath, a tensioning rod, a tensioning nut rotatable on the tensioning rod, an inner spring configured to actuate the collet in a first direction, and an outer spring configured to actuate the tensioning rod in a second direction, the second direction being opposite to the first direction.

21 Claims, 10 Drawing Sheets

(56) References Cited

U.S. PATENT DOCUMENTS

| | | | | |
|---|---|---|---|---|
| 2003/0181934 A1* | 9/2003 | Johnston | A61B 17/162 | 606/167 |
| 2005/0081946 A1* | 4/2005 | Koons | B21F 15/00 | 140/123.5 |
| 2005/0240191 A1* | 10/2005 | Albertson | A61B 17/8076 | 606/75 |
| 2005/0240198 A1* | 10/2005 | Albertson | A61B 17/8076 | 606/103 |
| 2010/0191257 A1* | 7/2010 | Boulnois | A61B 17/128 | 606/143 |
| 2011/0011579 A1* | 1/2011 | Wells | E21B 10/62 | 166/217 |
| 2012/0065638 A1* | 3/2012 | Moore | A61B 17/72 | 606/62 |
| 2012/0143225 A1* | 6/2012 | Chin | A61B 17/0401 | 606/148 |
| 2014/0371789 A1* | 12/2014 | Hariton | A61B 17/00234 | 606/215 |
| 2015/0127003 A1* | 5/2015 | Songer | A61B 17/8894 | 606/74 |
| 2015/0216523 A1* | 8/2015 | Marino | A61B 17/0401 | 606/232 |
| 2016/0270809 A1* | 9/2016 | Boudreaux | A61B 17/295 | |
| 2017/0108592 A1* | 4/2017 | Brockwell | H01J 5/32 | |
| 2017/0128114 A1* | 5/2017 | Songer | A61B 17/8872 | |
| 2017/0238983 A1* | 8/2017 | Kukla | A61B 17/885 | |

* cited by examiner

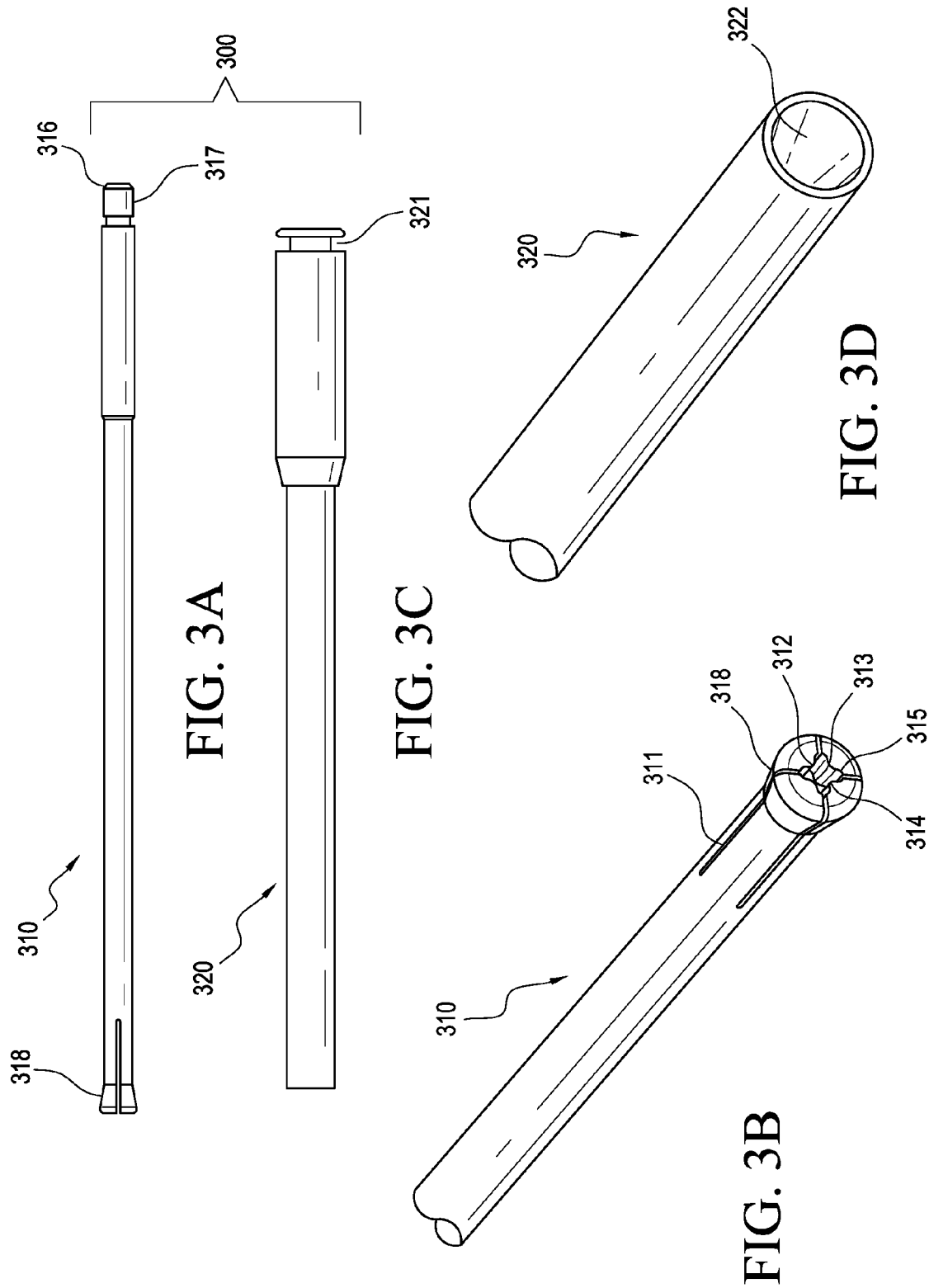

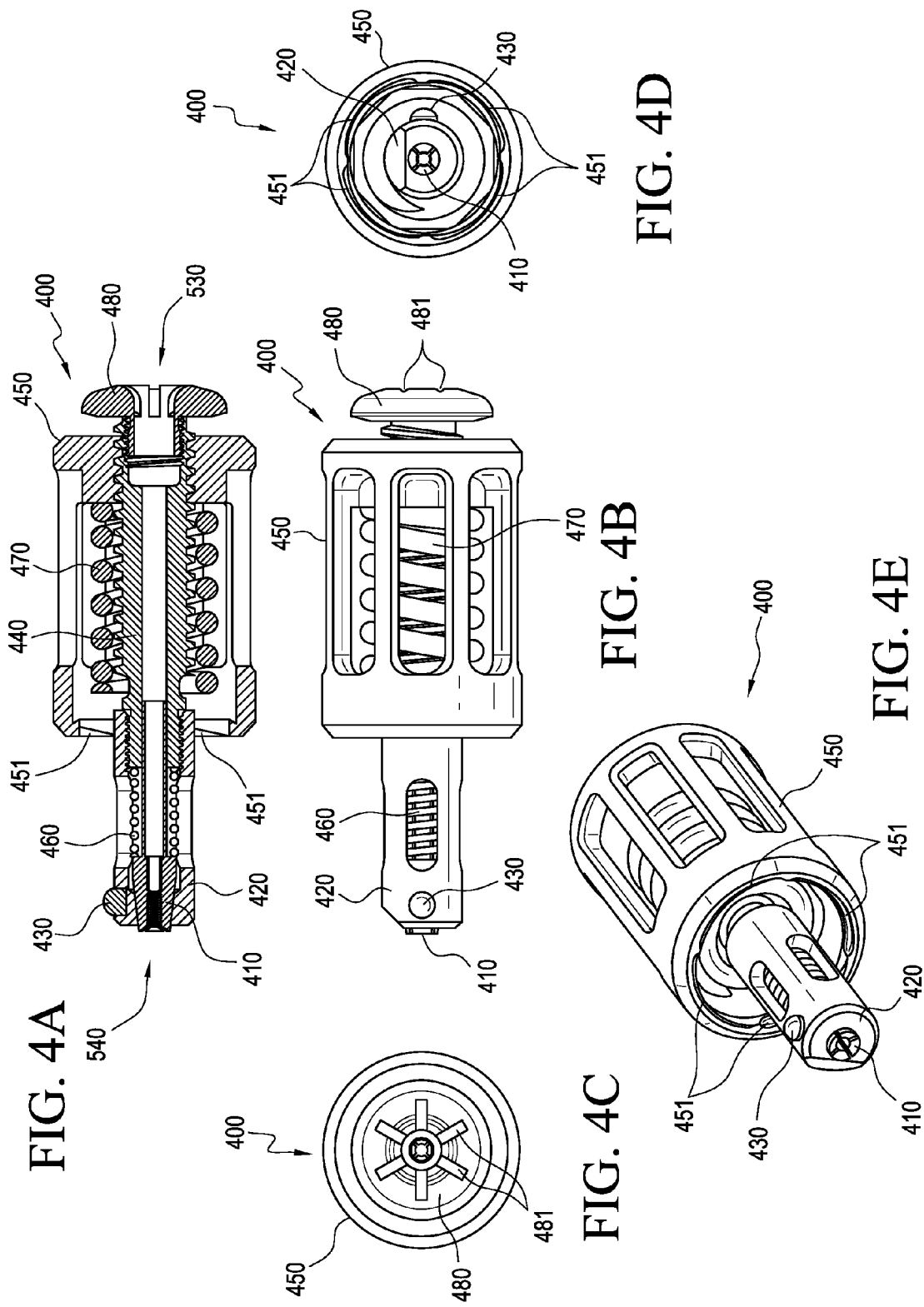

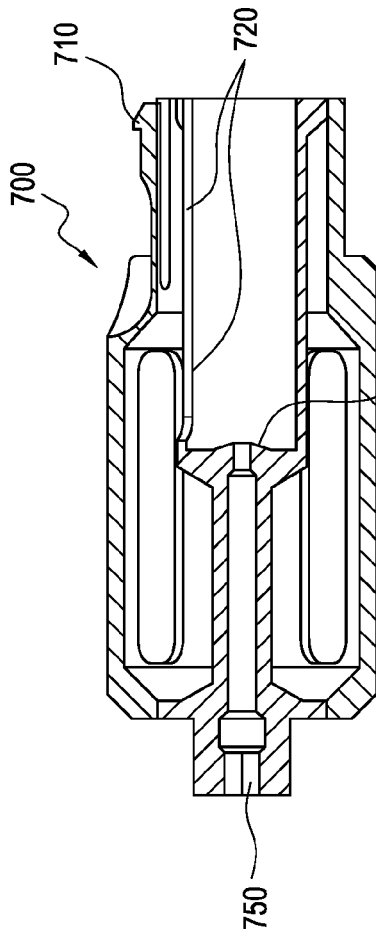
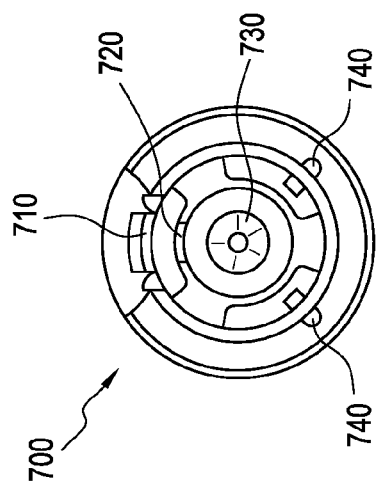
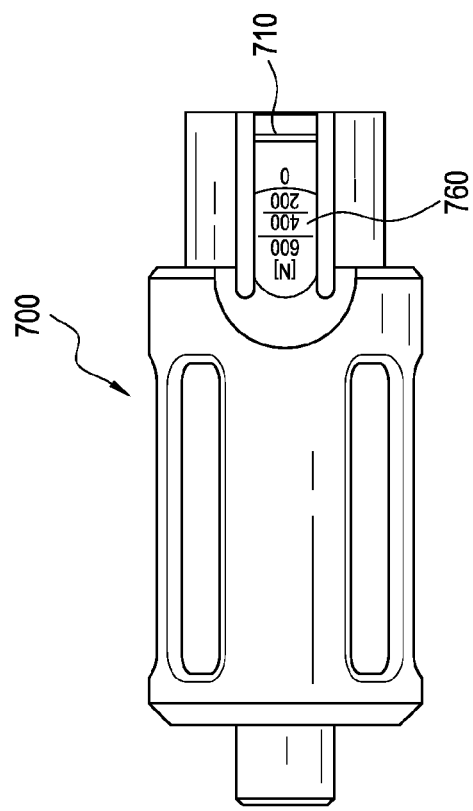
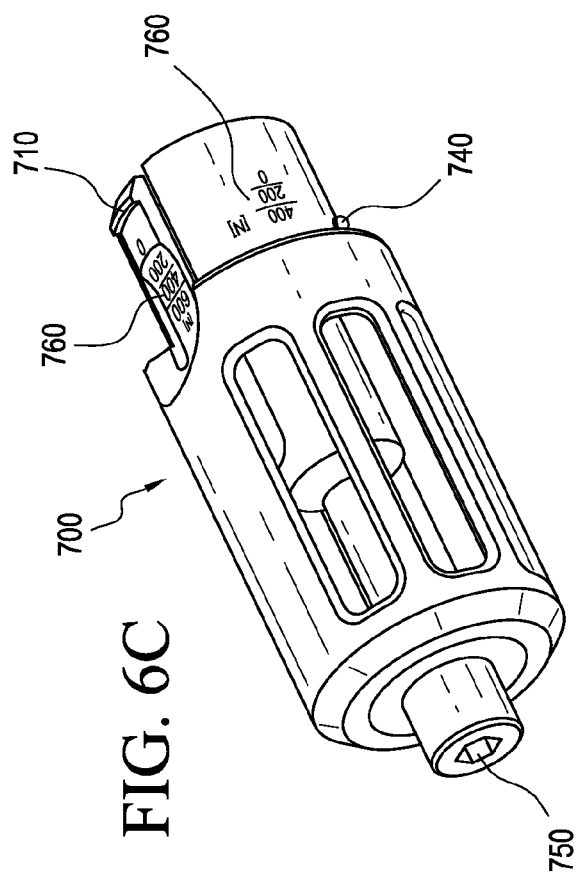
FIG. 6A
FIG. 6B
FIG. 6C
FIG. 6D

TENSIONING AND CRIMPING TOOL FOR ORTHOPEDIC CABLE TENSIONING

TECHNICAL FIELD

This disclosure relates generally to the tensioning and crimping of a cable, and more specifically, but not exclusively, to introducing tension onto orthopedic cables and fixating corresponding crimps on the tensioned cable to retain the cable tension.

BACKGROUND

During certain surgical procedures, specifically during orthopedic surgical procedures, it is a common requirement to anchor two or more elements together, such as pieces of a bone, two or more bones, or a combination of soft tissue and bone. This has been accomplished by a number of devices, such as bone bolts that penetrate two pieces of bone and use a nut to draw the segments together, bone screws and interconnecting plates, wires circling at least two pieces of bone, or sutures into the tissue.

Often such devices require a relatively large access opening through surrounding and/or covering tissue to implant and operate the anchoring devices. The enlarged access opening may increase patient pain and lengthen recovery time for the patient. Further, in some operation locations, it is difficult and impractical to make these large access openings to reach the appropriate site because of surrounding joints and blood vessels.

Cerclage systems provide an alternative to implants that must penetrate the bone to achieve fixation. These systems rely on passing a cable around two segments of bone and then tensioning, crimping and cutting the cable to squeeze the bone segments together. A significant drawback of these systems is that they require access around the entire bone.

SUMMARY OF EXEMPLARY EMBODIMENTS

A brief summary of various embodiments is presented below. Embodiments address the need to tension and crimp in-line orthopedic cables.

In order to overcome these and other shortcomings of the prior art and in light of the need for a tensioning tool and a crimping tool for introducing tension on an orthopedic cable and crimping a crimp onto an orthopedic cable, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments described herein relate to a tensioning and crimping tool for introducing tension on a cable and crimping a crimp onto the cable, the tensioning and crimping tool including a housing unit, a crimping section including a housing, a trigger-handle mounted to the housing, a crimping unit, including an inner crimping tube and an outer crimping tube, where the inner crimping tube is mounted inside the housing having a distal end configured to receive the cable and an outer crimping tube mounted around the inner crimping tube and configured to move in an axial direction relative to the inner crimping tube to crimp a crimp onto the cable when actuated by the trigger-handle, a tensioning section including the housing, a collet opener end at a proximal end of the inner crimping tube, and a tensioning unit including a collet axially positioned in a cone sheath, a tensioning rod having a proximal end connected to an end stop nut and a distal end connected to the cone sheath, a tensioning nut rotatable on the tensioning rod, an inner spring configured to actuate the collet in a first direction, and an outer spring configured to actuate the tensioning rod in a second direction, the second direction being opposite to the first direction.

In an embodiment of the present disclosure the housing unit includes the housing, the trigger-handle, a first bearing bolt, a knee lever, a second bearing bolt and a safety catch connected to the housing over the second bearing bolt configured to prevent the trigger-handle from actuating.

In an embodiment of the present disclosure the housing unit further includes a leaf spring configured to push the trigger-handle relative to the housing.

In an embodiment of the present disclosure, the outer crimping tube is configured to move towards the distal end when the trigger-handle is actuated and reaches a mechanical end stop when crimping stop bolts are in contact.

In an embodiment of the present disclosure, the cable is configured to pass through the inner crimping tube, the collet, the tensioning rod and the end stop nut.

In an embodiment of the present disclosure, the outer crimping tube is configured to move axially relative to the inner crimping tube.

In an embodiment of the present disclosure, the collet is configured to radially contract when the inner spring pushes the collet into the cone sheath.

In an embodiment of the present disclosure, rotation of the tensioning nut in a clockwise direction towards the distal end increases tension on the cable and rotation of the tensioning nut in a counter clockwise direction towards the proximal end decreases tension on the cable.

In an embodiment of the present disclosure, the tensioning unit further includes a guiding cam connected to the cone sheath.

In an embodiment of the present disclosure, the end stop nut includes a plurality of fixation slots on the proximal end of the end stop nut.

In an embodiment of the present disclosure, tension is configured to be applied to the cable on a first axis along the cable and crimping is configured to be applied to the cable on the first axis.

In an embodiment of the present disclosure, the trigger-handle is mounted to the housing over the first bearing bolt, the knee lever and the second bearing bolt.

In an embodiment of the present disclosure, tensioning stop slots at the distal end of the tensioning nut and the tensioning stop bolts in the housing interact to stop any axial displacement and rotation of the tensioning nut relative to the housing and prevent tensile force greater than 600N.

In an embodiment of the present disclosure, tensioning and crimping is uniaxial without radial deflection of the cable.

In an embodiment of the present disclosure, the length of the crimping section remains the same which creates constant tension in the cable.

In an embodiment of the present disclosure, the crimping unit is configured to be connected with a distal end of the housing unit.

In an embodiment of the present disclosure, the crimping unit is configured to be connected with the housing, where the outer crimping tube is guided on the inner crimping tube and secured axially by a tooth of the trigger-handle, and the inner crimping tube is connected to the housing over a coupling part at a proximal end of the inner crimping tube.

In an embodiment of the present disclosure, the crimping unit consists of an inner crimping tube and an outer crimping tube, where the inner crimping tube is made from a single part and the outer crimping tube is made from a single part.

In an embodiment of the present disclosure, the housing unit is configured to be connected with a distal end of the tensioning unit.

In an embodiment of the present disclosure, the housing unit is configured to be connected with a proximal end of the crimping unit.

In an embodiment of the present disclosure, the tensioning unit is configured to be connected with a proximal end of the housing unit.

Various embodiments described herein relate to a crimping section for crimping a crimp onto the cable, the crimping section including a housing, a trigger-handle mounted to the housing, and a crimping unit, including an inner crimping tube and an outer crimping tube, where the inner crimping tube is mounted inside the housing having a distal end configured to receive the cable, and the outer crimping tube is mounted around the inner crimping tube and is configured to move in an axial direction relative to the inner crimping tube to crimp a crimp onto the cable when actuated by the trigger-handle.

In an embodiment of the present disclosure, the outer crimping tube is configured to move towards the distal end when the trigger-handle is actuated and reaches a mechanical stop when crimping stop bolts are in contact.

In an embodiment of the present disclosure, the length of the crimping section remains the same which creates constant tension in the cable.

In an embodiment of the present disclosure, the outer crimping tube is configured to move axially relative to the inner crimping tube.

In an embodiment of the present disclosure, the trigger-handle is mounted to the housing over the first bearing bolt, the knee lever and the second bearing bolt.

In an embodiment of the present disclosure, the crimping unit consists of an inner crimping tube and an outer crimping tube, where the inner crimping tube is made from a single part and the outer crimping tube is made from a single part.

Various embodiments described herein relate to a tensioning section for tensioning the cable, the tensioning section including a housing, a collet opener end as part of a proximal end of the inner crimping tube, and a tensioning unit, including a collet axially positioned in a cone sheath, a tensioning rod having a proximal end connected to an end stop nut and a distal end connected to the cone sheath, a tensioning nut rotatable on the tensioning rod, an inner spring configured to actuate the collet in a first direction, and an outer spring configured to actuate the tensioning rod in a second direction, the second direction being opposite to the first direction.

In an embodiment of the present disclosure, the tensioning section further includes the tensioning unit further including a guiding cam connected to the cone sheath.

In an embodiment of the present disclosure, the cable is configured to pass through the inner crimping tube, the collet, the tensioning rod and the end stop nut.

In an embodiment of the present disclosure, the collet is configured to radially contract when the inner spring pushes the collet into the cone sheath.

In an embodiment of the present disclosure, rotation of the tensioning nut in a clockwise direction towards the distal end increases tension on the cable and rotation of the tensioning nut in a counter clockwise direction towards the proximal end decreases tension on the cable.

In an embodiment of the present disclosure, the end stop nut includes a plurality of fixation slots on the proximal end of the end stop nut.

In an embodiment of the present disclosure, tension is configured to be applied to the cable on a first axis and crimping is configured to be applied to the cable on the first axis.

In an embodiment of the present disclosure, tensioning stop slots at the distal end of the tensioning nut and the tensioning stop bolts in the housing interact to stop any axial displacement and rotation of the tensioning nut relative to the housing and prevent tensile force greater than 600N.

In an embodiment of the present disclosure, tensioning is smooth and stepless between 0 and 600N of a cable.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the invention are more fully disclosed in the following specification, reference being had to the accompanying drawings, in which:

FIG. 3A illustrates a side view of the inner crimping tube;

FIG. 3B illustrates a view of the distal end of the inner crimping tube;

FIG. 3C illustrates a side view of the outer crimping tube

FIG. 3D illustrates a view of the distal end of the outer crimping tube;

FIG. 4A is a sectional side view of the tensioning unit;

FIG. 4B is a top view of the tensioning unit;

FIG. 4C is a proximal view of the tensioning unit;

FIG. 4D is a distal view of the tensioning unit;

FIG. 4E is a perspective view of the tensioning unit;

FIG. 6A is a proximal view of the tensioning grip;

FIG. 6B is a sectional side view of the tensioning grip;

FIG. 6C is a perspective view of the tensioning grip;

FIG. 6D is a top view of the tensioning grip.

Figure 1A:
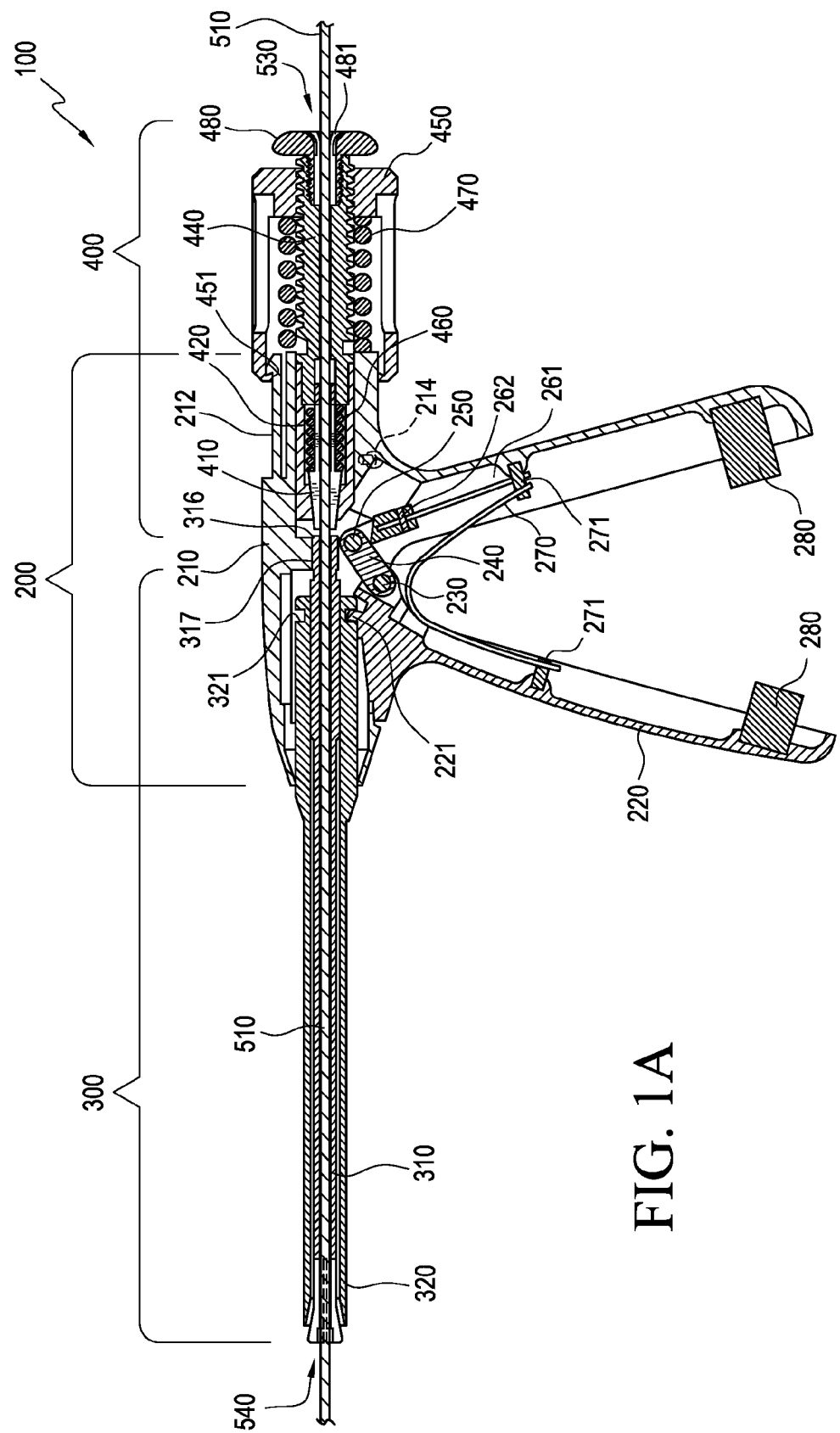
FIG. 1A is a sectional side view of the tensioning and crimping tool.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION OF THE INVENTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable.

The tensioning and crimping tool 100 provides a convenient and effective system for securing two segments of bone together while operating on a single axis. Such a system may be operable through a relatively small insertion opening or openings to securely hold two bone segments together.

The tensioning and crimping tool 100 is a pistol shaped, two-hand operable tensioning and crimping device which functions to first introduce tension onto a cable 510 and second to fixate a corresponding crimp 520 on the cable 510.

The tensioning and crimping tool 100 is a multi-use tool which is capable of applying tension of up to 600N and crimping a crimp 520 onto the cable 510 of up to 2.0 millimeter in diameter.

Embodiments of the tensioning and crimping tool 100 are described below, including the two components of the tensioning and crimping tool 100 which include the tensioning section and the crimping section.

FIG. 1A illustrates a sectional side view of the tensioning and crimping tool 100 which includes the housing unit 200, the crimping unit 300 and the tensioning unit 400.

The tensioning and crimping tool 100 includes a distal end 540 and a proximal end 530, with the cable 510 being inserted into the distal end 540 of the tensioning and crimping tool 100 and the cable 510 exiting the proximal end 530 of the tensioning and crimping tool 100.

The crimping section may include a housing 210, a trigger-handle 220 mounted to the housing 210 by a first bearing bolt 230, a knee lever 240 and a second bearing bolt 250.

Finally, the crimping section may also include a crimping unit 300, including an inner crimping tube 310 mounted inside the housing 210 having a distal end 540 configured to receive the cable 510 and an outer crimping tube 320 mounted around the inner crimping tube 310 and configured to move in an axial direction relative to the inner crimping tube 310 to crimp a crimp 520 onto the cable 510 when actuated by the trigger-handle 220.

The housing unit 200 may include a housing 210, a trigger-handle 220, a first bearing bolt 230, a knee lever 240, a second bearing bolt 250, a safety catch 260 connected to the housing 210 by the second bearing bolt 250 configured to prevent the trigger-handle 220 from actuating.

Finally, the housing unit 200 further includes a leaf spring for trigger-handle 270 configured to push the trigger-handle 220 relative to the housing 210.

The tensioning section may include a housing 210 and a collet opener end 316 at the proximal end of the inner crimping tube 310.

Finally, the tensioning section may also include a tensioning unit 400, including a cone sheath 420, a collet 410 which is axially displaceable in the cone sheath 420, a guiding cam 430 which is connected to the cone sheath 420, a tensioning rod 440 which is connected to the cone sheath 420, a tensioning nut 450 which is rotatable on the tensioning rod 440, an inner spring 460 which is positioned between the collet 410 and the tensioning rod 440, an outer spring 470 which is positioned between the proximal end 530 of the housing 210 and the tensioning nut 450, and an end-stop nut 480 which is mounted to the tensioning rod 440.

Figure 1B:
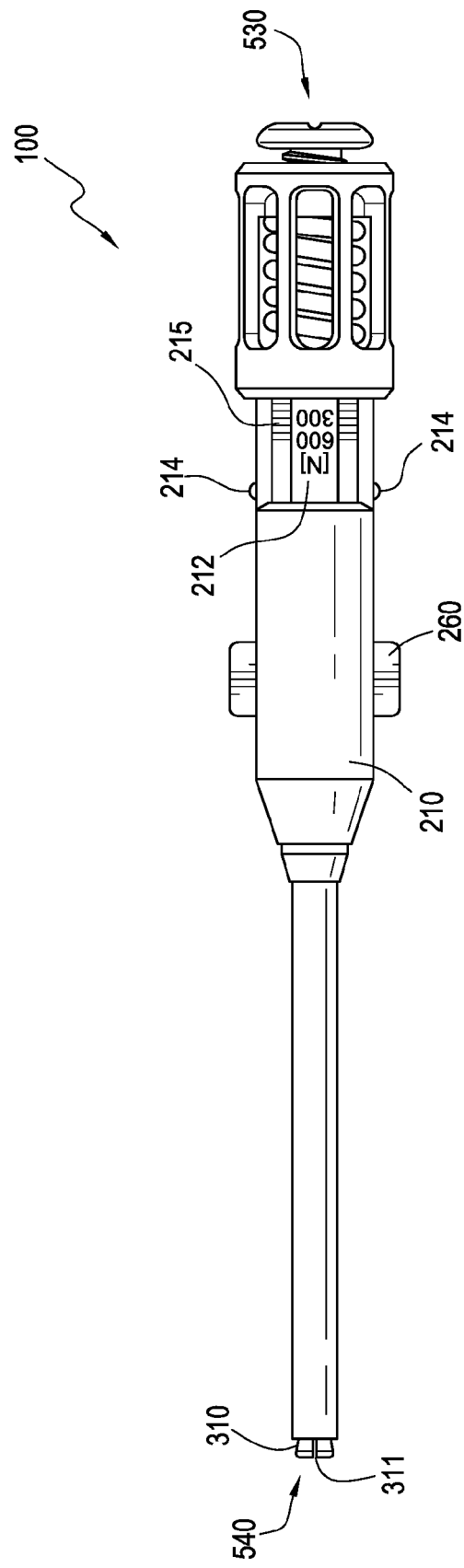
FIG. 1B is a top view of the tensioning and crimping tool.

FIG. 1B illustrates a top view of the tensioning and crimping tool 100, further including the safety catch 260 which prevents the trigger-handle 220 from actuating. In order for the trigger-handle 220 to actuate, the safety catch 260 must be pressed in the downward direction.

Figure 1C:
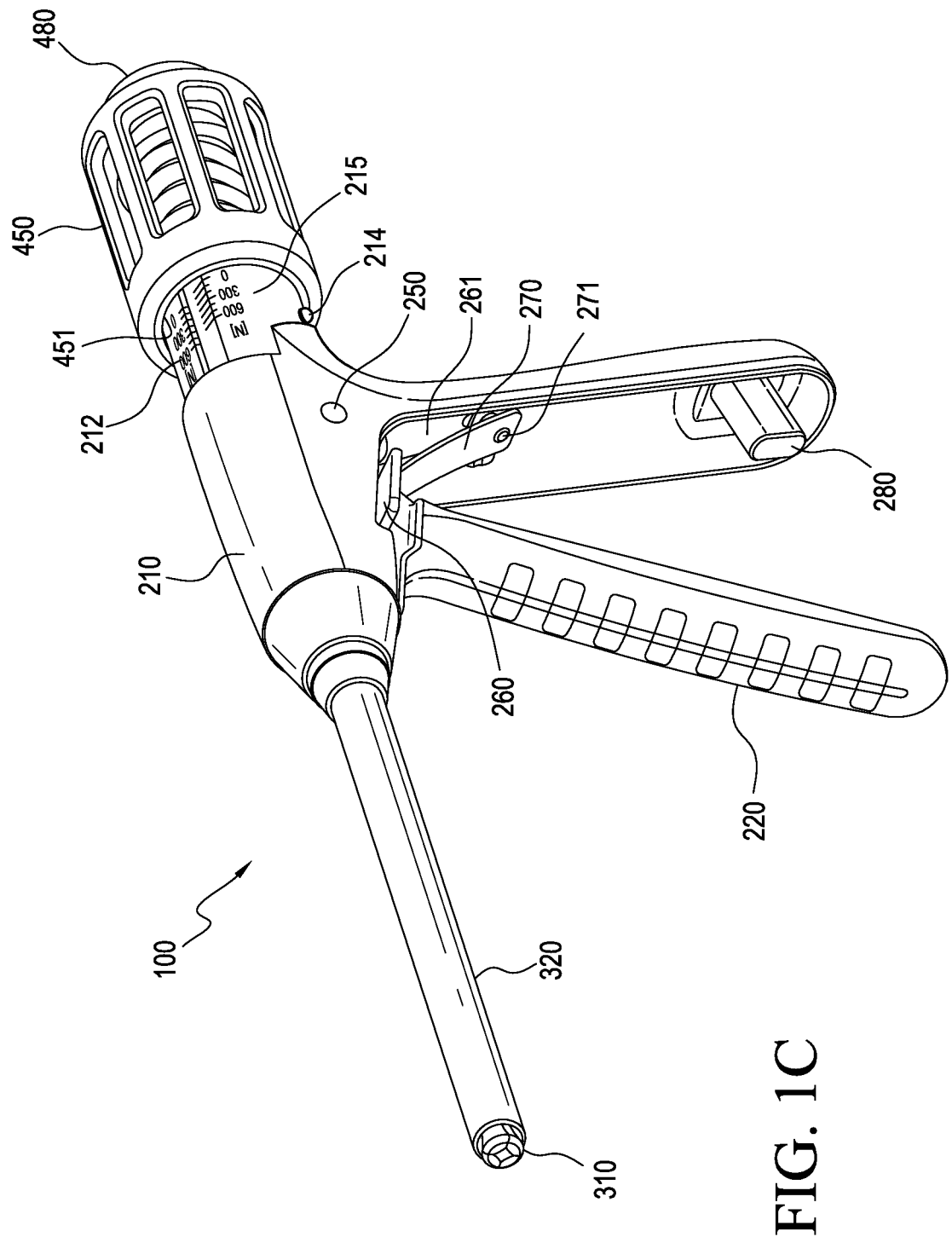
FIG. 1C is a perspective view of the tensioning and crimping tool.

FIG. 1C illustrates a perspective view of the tensioning and crimping tool 100.

In order to operate the tensioning and crimping tool 100 to tension and crimp a crimp 520 onto the cable 510, the tensioning and crimping tool 100 must be brought into the reset position which is defined as the proximal end 530 of the tensioning nut 450 being in contact with the distal end 540 of the end-stop nut 480 and the safety catch 260 is engaged with the guiding bolts 222 of the trigger-handle 220.

In the reset position, the collet 410 is in direct contact with the collet opener end 316 of the inner crimping tube 310, and when the collet 410 is pushed towards the collet opener end 316 with the cone sheath 420, the collet 410 is opened which allows a cable 510 to freely pass through the tensioning and crimping tool 100, as will be described in further detail below.

Once the tensioning and crimping tool 100 is in the reset position, the cable 510 can be inserted through the center hole of the inner crimping tube 310 on the distal end 540 of the tensioning and crimping tool 100 where the inner crimping tube 310 protrudes from the outer crimping tube 320.

After the cable 510 has entered the tensioning and crimping tool 100 through the center hole of the inner crimping tube 310, the collet 410, the tensioning rod 440 and the end-stop nut 480, the cable 510 exits the tensioning and crimping tool 100 at the end-stop nut 480.

Once the cable 510 is positioned in the tensioning and crimping tool 100, the cable 510 may be guided through the tensioning and crimping tool 100 to position it to the necessary length and at the required place where the crimp 520 has to be crimped onto the cable 510.

Once the crimping begins, there is no further change to the length of the tensioning and crimping tool 100 which ensures a constant cable length and thus a constant tension in the cable 510.

In an embodiment of the present disclosure, the tensioning and crimping tool 100 may be configured to crimp a crimp 520 onto the cable 510 without previously tensioning the cable 510.

In the above embodiment, in order to operate crimping, in which the tensioning and crimping tool 100 is configured to crimp a crimp 520 on the cable 510, the safety catch 260 has to be released by pushing it in the downward direction, in order to allow the trigger-handle 220 to actuate.

Once the safety catch 260 has been released, the trigger-handle 220 is actuated to the crimping stop bolts 280. During the actuation of the trigger-handle 220, the inner cone 322 of the outer crimping tube 320 is axially displaced to the outer cone 318 of the inner crimping tube 310, leading to the distal end 540 of the inner crimping tube 310 constricts to a smaller diameter which introduces a plastic deformation of the crimp 520 on the cable 510, which results in a fixation of the crimp 520 on the cable 510 and allows for in-line crimping action and further prevents any radial deflection of the cable. Once the crimp 520 is crimped on the cable 510 by the trigger-handle 220 after reaching the crimping stop bolts 280, the crimping action is completed. The crimping stop bolts 280 are positioned at the end of the trigger-handle 220 and the housing 210.

After relieving of the trigger handle 220 by the leaf-spring for trigger-handle 270 and the self-engagement of the safety catch 260 by the leaf-spring for safety catch 261 over the guiding bolts 222 of the trigger-handle 220 and the proximal end 530 of the tensioning nut 450 being in contact with the distal end 540 of the end-stop nut 480 (reset position), the tensioning and crimping tool 100 can be removed over and from the cable 510.

In summary, the crimping section is in reset position, the safety catch 260 is pressed, a crimping action is performed, there is a relief of the crimping action (by the leaf-spring for trigger-handle 270), self-engagement of the safety catch 260 (by the leaf-spring for safety catch 261) and finally return to the reset position. Appropriate markings on the crimping section may guide through this process.

In another embodiment of the present disclosure, the tensioning and crimping tool 100 may be configured to first tension the cable 510 and then subsequently a crimp 520 can be crimped on the tensioned cable 510.

In the above embodiment, in order to operate tensioning, the tensioning and crimping tool 100 may apply a tension onto the cable 510 before crimping, which is performed by the cable 510 being grasped by rotating the tensioning nut 450 in clockwise direction out of the reset position, away from the end-stop nut 480, towards a distal end 540.

A tensile force of up to 600N can be introduced onto the cable 510 by rotating the tensioning nut 450 in clockwise direction further away, from the end-stop nut 480, towards a distal end 540. The tensile force corresponds to the axial compression of the outer spring 470 and thus, to the axial displacement of the tensioning nut 450 relative to the housing 210.

At the related axial displacement of 600N, the tensioning stop slots 451 of the tensioning nut 450 and the tensioning stop bolts 214 of the housing 210 interact and stop any further axial displacement and rotation of the tensioning nut 450 relative to the housing 210 and thus, any further increase of tensile force higher than 600N.

The tensioning stop bolts 214 may be rounded with a spherical head to prevent injury of the skin during holding and movement of the tensioning and crimping tool 100.

It is the above axial displacement which is used to visualize the adjusted tensile force with a corresponding etched scale 215 on the housing 210. The etched scale 215 on the housing 210 may show the amount of tensile force on the cable 510 as the tensioning nut 450 moves relative to the housing 210. After reaching the necessary tension force, the crimping action, which is described above, may be performed.

Once the tension has been applied and the crimp 520 has been crimped onto the cable 510, the tensioning and crimping tool 100 can relieve the tension by rotating the tensioning nut 450 in counter clockwise direction towards the end-stop nut 480, towards the proximal end 530, until the above described reset position is reached.

During the relieve action, the above process of tensioning the cable 510 by grasping and tensioning proceeds in the reverse direction.

Once the reset position has been reached, the tensioning and crimping tool 100 can be removed over and from the cable 510.

In summary, tensioning the cable 510 begins with the tensioning section being in the reset position, then grasping the cable 510, tensioning the cable 510, relieving the tension on the cable 510, and then returning to the reset position. Appropriate markings 490 on the tensioning unit 400 may guide through this process.

After using the tensioning and crimping tool 100, the crimping unit 300, including the inner crimping tube 310 and the outer crimping tube 320 and the tensioning unit 200 as one single element can be removed from the housing unit 200.

The housing 210, the trigger-handle 220, the safety catch 260 and the tensioning unit 400 are configured such that the device can be operable by a right-handed user as well as a left-handed user.

The housing 210 and the tensioning unit 400 are coupled using a leaf-clip 212 which allows for detachment of the housing 210 from the tensioning unit 400. The coupling between the housing 210 and the crimping unit 300 can be a threaded joint or clip which allows for quick coupling and decoupling.

The housing unit 200 includes the knee lever 240 which transmits and amplifies the force applied by hand into the required crimping force. The axial movement induced from a tooth 221 onto a radial flute 321 (see FIG. 2A-B) generates a force which is used for crimping. The force could also be used to generate a saw or a clamp, depending on the working unit of any kind attached to the housing unit 200.

Figure 2B:
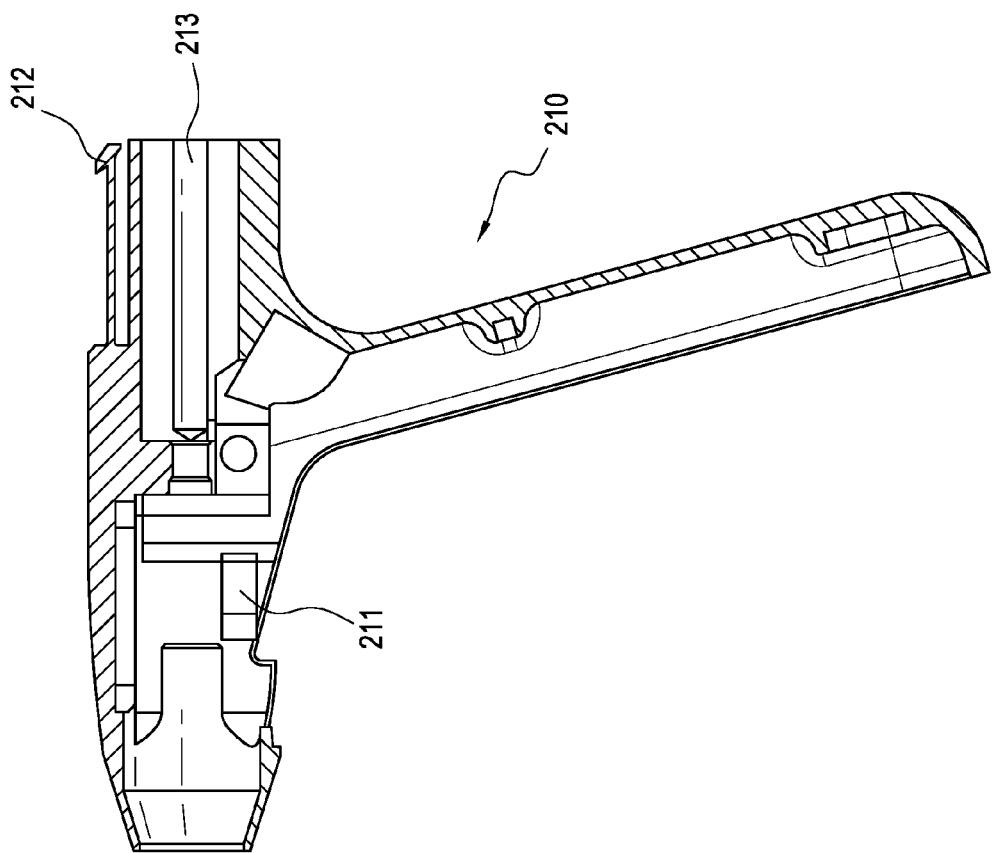
FIG. 2B illustrates a sectional side view of the housing.
Figure 2A:
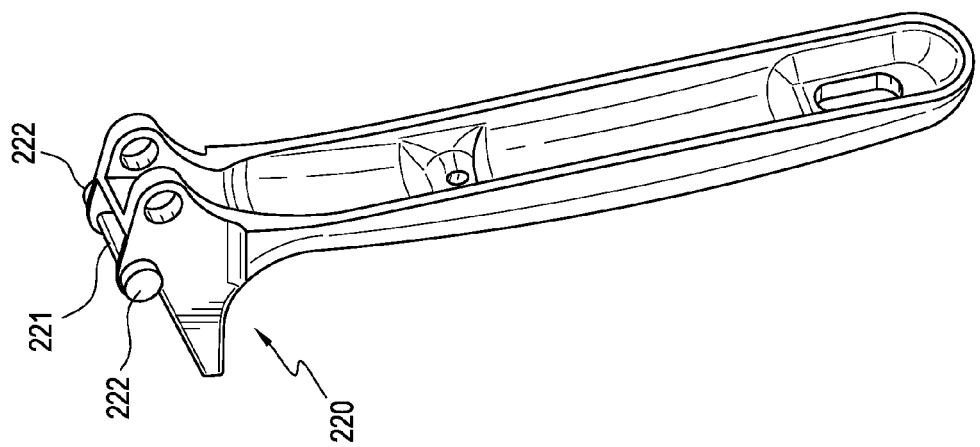
FIG. 2A illustrates a view of the trigger-handle.

FIG. 2A illustrates a view of the trigger-handle 220 and FIG. 2B illustrates a sectional side view of the housing 210.

While pulling on the trigger-handle 220, the trigger-handle 220 is led by two guiding bolts 222 interacting with two guiding slots 211 in the housing 210. During this movement, the tooth 221 of the trigger-handle 220 interacts with the radial flute 321 (see FIG. 3C) of the outer crimping tube 320, which works similar to an involute gear and pushes the outer crimping tube 320 in a distal direction when the trigger-handle 220 is squeezed.

The housing 210 has a leaf-clip 212 at the proximal end 530 and a notch 213 fitting the outer geometry of the cone sheath 420 and the guiding cam 430 of the tensioning unit 400.

The housing 210 and the trigger-handle 220 can be manufactured using investment casting.

FIG. 3A illustrates a side view of the inner crimping tube 310. The inner crimping tube 310 may be different lengths depending on the type of intervention required. The inner crimping tube 310 may be different diameters depending on the type of intervention required. Finally, the inner crimping tube 310 may be different materials (such as x-ray visible) depending on the type of intervention required.

At the distal end 540 of the inner crimping tube 310 is the outer cone 318 of the inner crimping tube 310. At the proximal end 530 of the inner crimping tube 310 are the coupling part 317 and the collet opener end 316.

FIG. 3B illustrates a view of the distal end 540 of the inner crimping tube 310 being made of a single piece of material. The slot 311 is used and implemented to get the functionality of a flexure bearing of the distal end 540 of the inner crimping tube 310. The crimping mold 312 deforms the round crimp 520 resulting in a crimped crimp 520. The seating 313 extends inward as part of the crimping mold 312. The primary crimping mold 314 structure deforms the material of the crimp 520 onto the cable 510. The secondary crimping mold 315 structure allows the expansion of the crimped material and its deformation which is not directly in contact with the cable 510.

FIG. 3C illustrates a side view of the outer crimping tube 320. The outer crimping tube 320 may be different lengths depending on the type of intervention required. The outer crimping tube 320 may be different diameters depending on the type of intervention required. Finally, the outer crimping tube 320 may be different materials (such as x-ray visible) depending on the type of intervention required.

The outer crimping tube 320 includes a radial flute 321 where the tooth 221 (see FIG. 2A) of the trigger-handle 220 interacts, which works similar to an involute gear and pushes the outer crimping tube 320 in a distal direction when the trigger-handle is squeezed.

FIG. 3D illustrates a view of the distal end of the outer crimping tube 320 being made of a single piece of material with an inner cone 322, which is able to deform the outer cone 318 of the inner crimping tube 310.

During actuation of the trigger-handle 220, the inner cone 322 of the outer crimping tube 320 is axially displaced to the outer cone 318 of the inner crimping tube 310. This leads to the radial constriction of the outer cone 318 of the inner crimping tube 310 and thus to the crimping of the crimp 520.

The outer crimping tube 320 is inserted through a hole on the distal end 540 of the housing 210 where the proximal radial flute 321 of the outer crimping tube 320 is in contact with the tooth 221 of the trigger-handle 220.

The inner crimping tube 310 is inserted through the outer crimping tube 320 and connected to the housing 210 over the coupling part 317 through a screwing operation. As the outer crimping tube 320 is guided on the inner crimping tube 310, the outer crimping tube 320 cannot deflect in a radial direction.

The crimping section operates such that the crimping action is performed by having the inner crimping tube 310 being fixed to the housing 210 and the outer crimping tube 320 moving axially.

FIG. 4A-E illustrates different views of the tensioning unit 400. The tensioning unit 400 includes an end-stop nut 480 on the proximal end 530 of the tensioning unit 400. The end-stop nut 480 includes a plurality of fixation slots 481 which are grooves on the end-stop nut 480 configured to receive and hold the cable 510 in place during tensioning and crimping.

Figure 4F:
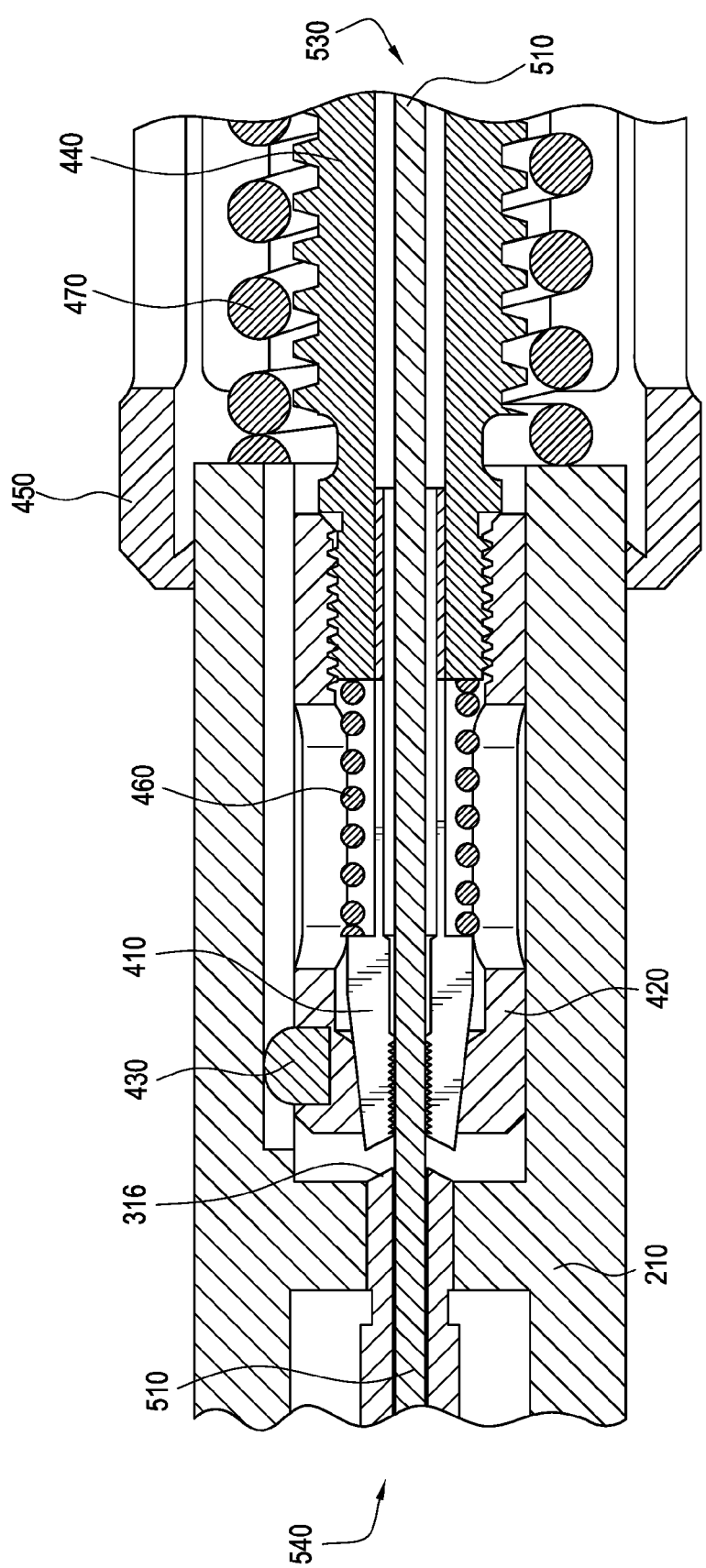
FIG. 4F is a sketched sectional side view of the tensioning section.

FIG. 4F illustrates a sketched sectional side view of the tensioning section. The tensioning section includes the housing 210, the collet opener end 316 and the tensioning unit 400 (see FIG. 4A-E), including a collet 410, a tensioning rod 440, an outer spring 470, an inner spring 460, a cone sheath 420, a guiding cam 430, a tensioning nut 450 and an end-stop nut 480 (see FIG. 4A-E).

FIG. 4F illustrates the cable 510 being tensioned. During the initial turn of the tensioning nut 450 in clockwise direction, out of the reset position, away from the end-stop nut 480, the inner spring 460 pushes the collet 410 into the cone sheath 420, which leads to a radial contraction of the collet 410, which leads to a grasping of the cable 510.

When the tensioning nut 450 is turned further in clockwise direction, further away from the end-stop nut 480, towards a distal end 540, the collet 410 loses direct contact with the collet opener end 316 resulting in a self-retaining mechanism because of the further expansion of the inner spring 460 and the friction forces between the cable 510 and the collet 410 and because of the geometry of the cone-angle between the collet 410 and the cone sheath 420.

Because the tensioning rod 440 is attached to the cone sheath 420, when the tensioning nut 450 is rotated in clockwise direction which compresses the outer spring 470, the tensioning rod 440 and the cone sheath 420 are pulled towards the proximal end 530, however, during this rotation, the self-retaining mechanism increases and pulls the collet 410 through the distal end 540 of the cone sheath 420, which, because of the cone-shape of the cone sheath 420, causes the collet 410 to create more radial contraction on the cable 510 and further applies tension to the cable 510.

Once tension has been applied, it is impossible to pull the cable 510 towards the distal end 540 because this pulls the collet 410 deeper into the cone sheath 420 increasing the self-retaining mechanism and the clamping force on the cable 510; however, pulling the cable 510 towards a proximal end 530 is still possible because this pulls the collet 410 out of the cone sheath 420 and against the inner spring 460 decreasing the self-retaining mechanism and the clamping force on the cable 510.

Due to this self-retaining mechanism, the tensioning section is able to apply pre-tensioning of the cable 510 by pulling directly on the cable 510 as soon as the tensioning and crimping tool 100 is not in the reset position. The pre-tensioning is able to be performed manually if the pulling force applied manually is higher than the actual tensioning force.

Figure 4G:
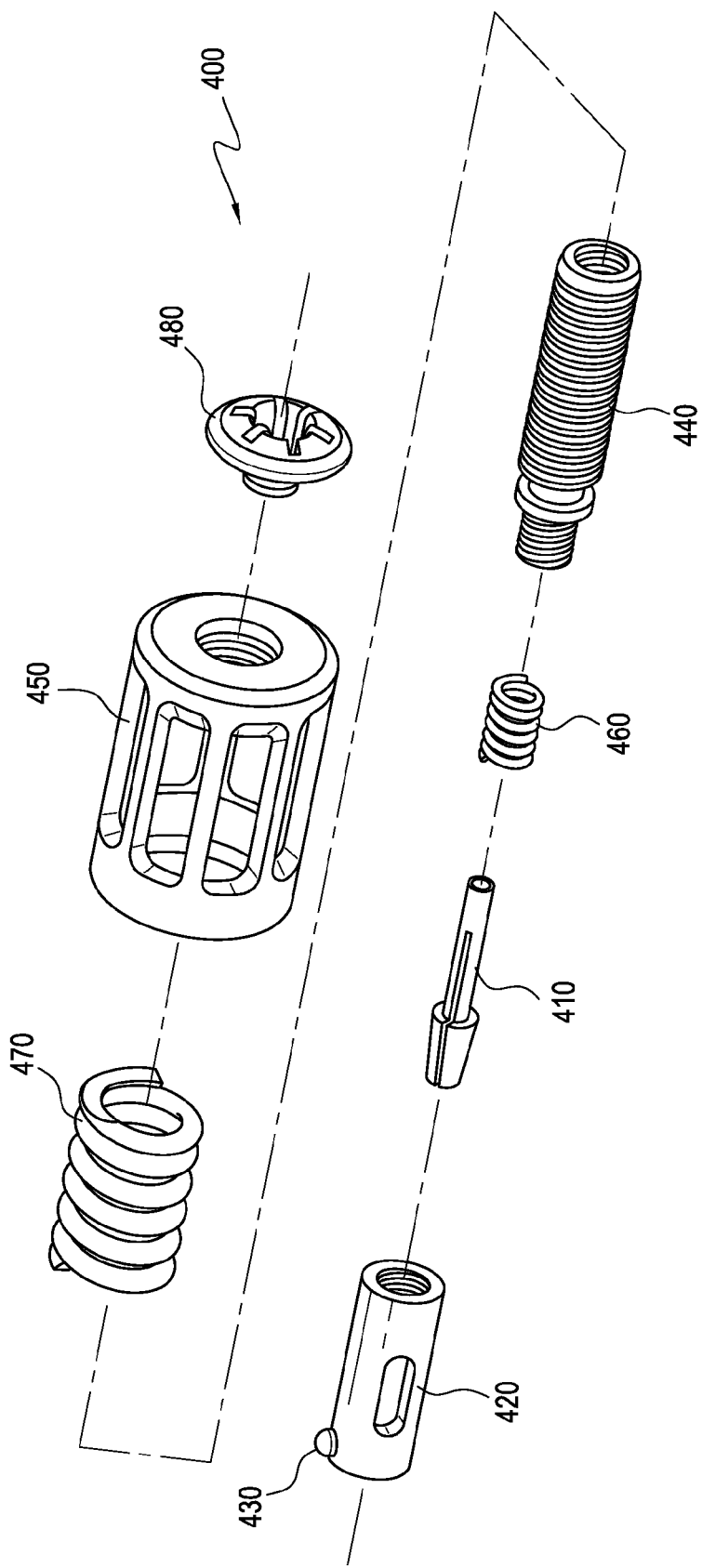
FIG. 4G is an exploded view of the tensioning unit.

FIG. 4G illustrates an exploded view of the tensioning unit 400, the tensioning unit 400 including a cone sheath 420, a collet 410, an inner spring 460, a tensioning rod 440, an outer spring 470, a tensioning nut 450 and an end-stop nut 480.

The collet 410 may be made from a single piece of material, which may be a flexure bearing and which may be flexible and easily deformable. With the added flexibility, cables can be grasped and tensioned without producing a kink in the cable.

The tensioning and crimping tool 100 provides a smooth (step less) and faster tensioning and crimping of the cable 510 resulting in a shorter use time versus existing tools. The tensioning and crimping tool 100 also provides easier handling which reduces the attention that a user has to give to handling the tensioning and crimping tool 100. Further, the tensioning and crimping tool 100 facilitates two handed use which allows a single user to operate the tensioning and crimping tool 100. The tensioning and crimping tool 100 protects and covers the cable 510 and only a few components actually enter the patient, specifically, for the crimping unit 300, namely, the inner crimping tube 310 and the outer crimping tube 320, will become contaminated. Therefore, the crimping unit 300 is entirely decomposable for reprocessing. However, the tensioning unit 400 and the housing unit 200 are less likely to be contaminated and therefore can be thoroughly sanitized and used for the next procedure.

The tensioning and crimping tool 100 provides a ready to use system that does not require any assembly. This allows the user to immediately tension and crimp a crimp 520 onto the cable 510 after removal from the packaging. As the tensioning and crimping tool 100 is pre-assembled and pre-positioned, the user may use the system directly after boring a hole and inserting the cable 510.

Finally, the tensioning and crimping tool 100 allows for in-line tensioning and crimping of the cable 510 (i.e. both the tensioning and the crimping is being completed on the same axis), which allows minimally invasive surgery and further without any radial deflection of the cable during tensioning.

In another embodiment, a mini cable tensioner 600 is a rod-shaped, two hand operable tensioning device which is able to introduce tension onto a cable 510 for temporary fixation.

Figure 5A:
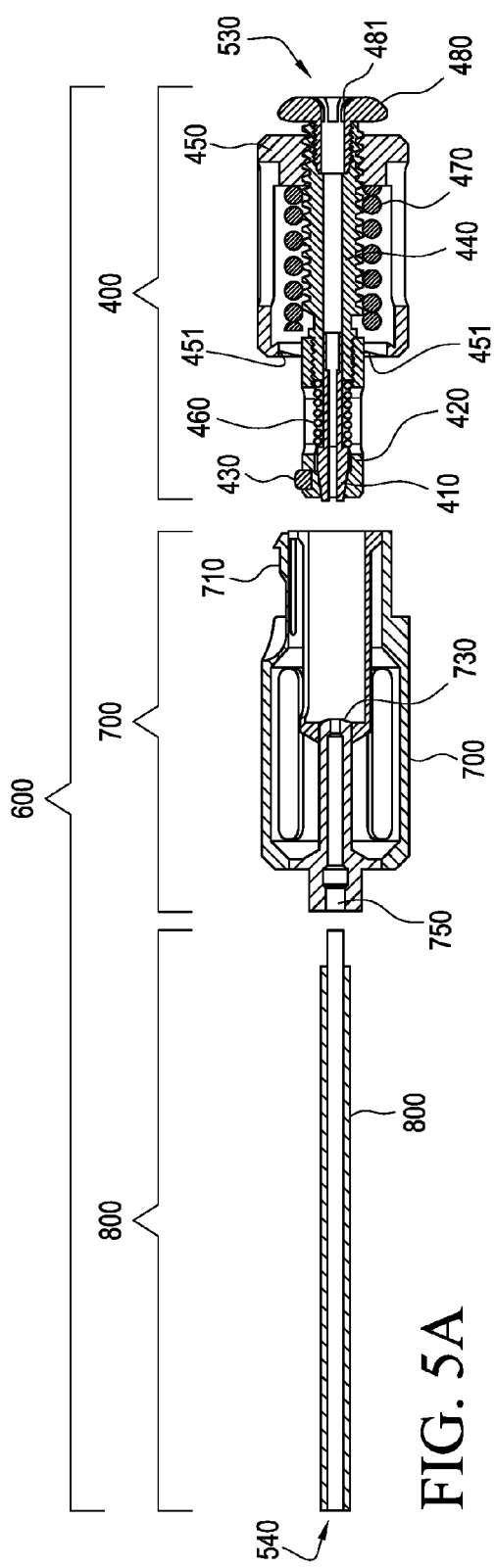
FIG. 5A is an exploded sectional side view of the mini cable tensioner.

FIG. 5A illustrates an exploded sectional side view of the mini cable tensioner 600. The mini cable tensioner 600 includes a tensioning unit 400, a tensioning grip 700 and a tensioning tube 800. The tensioning unit 400 corresponds to the above mentioned tensioning unit 400 and functions similarly to the above embodiment.

Figure 5B:
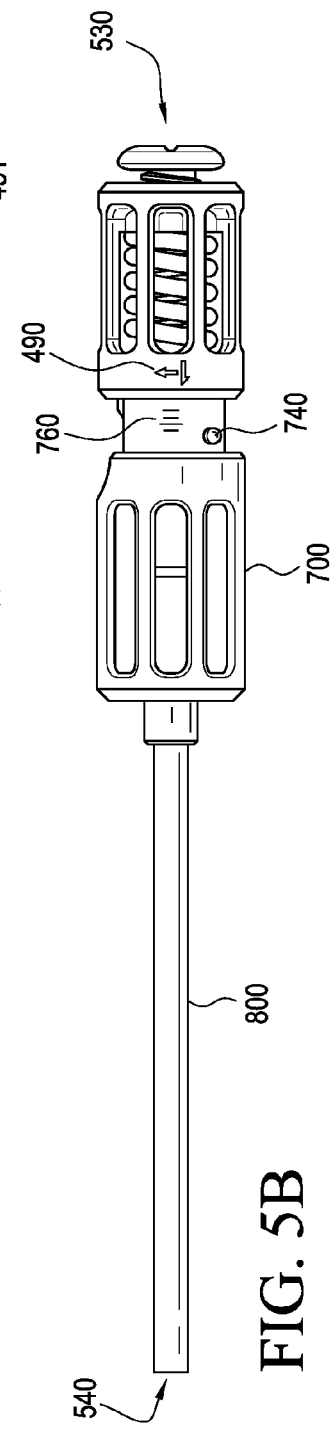
FIG. 5B is a side view of the mini cable tensioner.

FIG. 5B illustrates a side view of the mini cable tensioner 600. The mini cable tensioner 600 includes a distal end 540 and a proximal end 530, the cable 510 being inserted into the distal end 540 of the mini cable tensioner 600 and the cable 510 exiting the proximal end 530 of the mini cable tensioner 600.

Figure 5C:
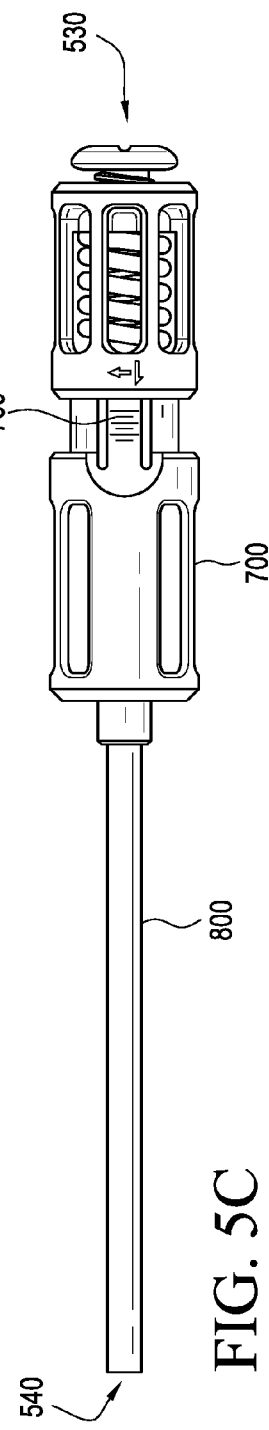
FIG. 5C is a top view of the mini cable tensioner.

FIG. 5C illustrates a top view of the mini cable tensioner 600.

The tensioning unit 400 may include a collet 410 which is axially displaceable in a cone sheath 420. The tensioning unit 400 may also include a guiding cam 430 which is connected to the cone sheath 420. The tensioning unit 400 may also include a tensioning rod 440 which is connected to the cone sheath 420 and a tensioning nut 450 which is movable by rotation in distal or proximal direction on the tensioning rod 440.

The tensioning unit 400 may also include an inner spring 460 which is positioned between the collet 410 and the tensioning rod 440 and an outer spring 470 which is positioned around the tensioning rod 440 between the proximal end 530 of the tensioning grip 700 and the tensioning nut 450.

The tensioning unit 400 may also include an end-stop nut 480 which is mounted to the proximal end 530 of the tensioning rod 440.

Finally, the tensioning unit 400 includes the end-stop nut 480 which includes a plurality of fixation slots 481 which are grooves on the end-stop nut 480 configured to receive and hold the cable 510 in place during cable handling, cable grasping and cable tensioning.

The tensioning unit 400 is able to apply pre-tensioning of the cable 510 by pulling directly on the cable 510 as soon as the mini cable tensioner 600 is not in the reset position. The pre-tensioning is able to be performed manually if the pulling force applied manually onto the cable 510 is higher than the actual tensioning force.

During the initial turn of the tensioning nut 450 in clockwise direction, out of the reset position, away from the end-stop nut 480, the cable 510 is immediately grasped and is smoothly tensioned by the tensioning unit 400.

The collet 410 may be made from a single piece of material, which may be a flexure bearing and which may be flexible and easily deformable. With the added flexibility, cables can be grasped and tensioned without producing a kink in the cable. For example, cables between 1.7 and 2.0 mm can be grasped and tensioned in-line without kinking. The mini cable tensioner 600 allows for in-line tensioning of the cable 510, which allows minimally invasive surgery and further prevents any radial deflection of the cable 510 during tensioning.

The tensioning grip 700 may be manufactured using three parts and may be configured such that the mini cable tensioner 600 can be operable by a right-handed user as well as a left-handed user.

The tensioning tube 800 may be straight or curved depending on the type of intervention required. The tensioning tube 800 may be different lengths depending on the type of intervention required. The tensioning tube 800 may be different diameters depending on the type of intervention required. The tensioning tube 800 may be different materials (such as x-ray visible) depending on the type of intervention required. The tensioning tube 800 may be able to transmit a torsional moment.

Finally, the mini-cable tensioner 600 includes the tensioning grip 700 and the tensioning unit 400 which are coupled using a leaf-clip 710 which allow for detachment of the tensioning unit 400 from the tensioning grip 700. The coupling between the tensioning grip 700 and the tensioning tube 800 can have a coupling-geometry 750 of a threaded joint or a snap-fit which allows for quick coupling and decoupling.

FIGS. 6A, 6C and 6D illustrate proximal, perspective, and top views, respectively, of the tensioning grip 700. The tensioning grip 700 is used as a handle and further used to connect the tensioning unit 400 at the proximal end 530 and the tensioning tube 800 at the distal end 540. The tensioning grip 700 can be made from three parts and has a leaf-clip 710 at the proximal end 530 and a notch 720 fitting the outer geometry of the cone sheath 420 and the guiding cam 430 of the tensioning unit 400.

The leaf-clip 710 allows for coupling between the tensioning grip 700 and the tensioning unit 400 and further allows for a stable axial and free rotational connection.

FIG. 6B illustrates a sectional side view of the tensioning grip 700. At the distal end 540 of the tensioning grip 700, the tensioning grip 700 has a coupling-geometry 750 to mount the tensioning tube 800 to the tensioning grip 700. The coupling-geometry 750 mates with the tensioning tube 800 in a complementary manner to fix the tensioning grip 700 and the tensioning tube 800 to one another. For example, the coupling-geometry 750 can be a hexagonal recess, which would mate with a hexagonal shaped end of the tensioning tube 800.

The tensioning tube 800 is mounted to the distal end 540 of the tensioning grip 700 inside the coupling-geometry 750, which allows for minimally invasive access to the intervention site.

In order to operate the mini cable tensioner 600, the mini cable tensioner 600 must be brought into the reset position which is defined as the proximal end 530 of the tensioning nut 450 is in contact with the distal end 540 of the end-stop nut 480.

In the reset position, the collet 410 is in direct contact with the collet opener 730 and when the collet is pushed towards the collet opener 730 with the cone sheath 420, the collet 410 is opened which allows a cable 510 to freely pass through the mini cable tensioner 600, as will be described in further detail below.

Once the mini cable tensioner 600 is in the reset position, the cable 510 can be inserted through the distal end 540 of the tensioning tube 800.

After the cable 510 has entered the mini cable tensioner 600 through the tensioning tube 800, the tensioning grip 700, the collet 410, the tensioning rod 440 and the end-stop nut 480, the cable 510 exits the mini cable tensioner 600 at the proximal end 530 of the end-stop nut 480.

Once the cable 510 is positioned in the mini cable tensioner 600, the cable 510 can be guided through the mini cable tensioner 600 to position it to the necessary length and at the required place where the tension has to be applied onto the cable 510.

In the above embodiment, the mini cable tensioner 600 can apply tension onto the cable 510 by the cable 510 being grasped by rotating the tensioning nut 450 in clockwise direction out of the reset position and away from the end-stop nut 480, towards a distal end 540.

The inner spring 460 pushes the collet 410 into the cone sheath 420 which leads to a radial contraction of the collet 410 and to the cable 510 being grasped.

When the tensioning nut 450 is rotated further in clockwise direction, away from the end-stop nut 480, towards a distal end 540, the collet 410 loses direct contact with the collet opener 730 at the bottom of the notch 720 of the tensioning grip 700, a self-retaining mechanism arises because of the further expansion of the inner spring, the friction forces between the cable 510 and the collet 410 and because of the geometry of the cone-angle between the collet 410 and the cone sheath 420.

Because the tensioning rod 440 is attached to the cone sheath 420, when the tensioning nut 450 is rotated in clockwise direction which compresses the outer spring 470, the tensioning rod 440 and the cone sheath 420 are pulled towards the proximal end 530, however, during this rotation, the self-retaining mechanism increases and pulls the collet 410 through the distal end 540 of the cone sheath 420, which, because of the cone-shape of the cone sheath 420, causes the collet 410 to create more radial contraction on the cable 510 and further applies tension to the cable.

Once tension has been applied, it is impossible to pull the cable 510 towards the distal end 540 because this pulls the collet 410 deeper into the cone sheath 420 increasing self-retaining mechanism and the clamping force on the cable 510; however, pulling the cable 510 towards a proximal end 530 is still possible because this pulls the collet 410 out of the cone sheath 420 and against the inner spring 460 decreasing the self-retaining mechanism and the clamping force on the cable 510.

A tensile force of up to 600N may be introduced onto the cable 510 by rotating the tensioning nut 450 in clockwise direction further away, from the end-stop nut 480, towards a distal end 540. The tensile force corresponds to the axial compression of the outer spring 470 and thus, to the axial displacement of the tensioning nut 450 relative to the tensioning grip 700.

At the related axial displacement of 600N, the tensioning stop slots 451 of the tensioning nut 450 and the tensioning stop bolts 740 of the tensioning grip 700 interact and stop any further axial displacement and rotation of the tensioning nut 450 relative to the tensioning grip 700 and thus, any further increase of tensile force higher than 600N.

It is the above axial displacement which is used to visualize the adjusted tensile force on the cable 510 via an etched scale 760 on the mini cable tensioner 600 (see FIG. 5C).

Once the required tension has been applied, the mini cable tensioner 600 can relieve the tension by rotating the tensioning nut 450 in counter clockwise direction towards the end-stop nut 480, towards the proximal end 530, until the above described reset position is reached.

During the relieve action, the above process of tensioning the cable 510 by grasping and tensioning proceeds in the reverse direction.

Once the reset position has been reached, the mini cable tensioner 600 can be removed over and from the cable 510.

After using the mini cable tensioner 600, the tensioning tube 800 and the tensioning unit 400 can be removed from the tensioning grip 700.

In summary, tensioning a cable with the mini cable tensioner 600 begins with the mini cable tensioner 600 being in the reset position, then grasping the cable 510, tensioning the cable 510, relieving the tension on the cable 510, and then returning to the reset position. Appropriate markings 490 on the tensioning unit 400 may guide through this process.

The mini cable tensioner 600 provides a smooth (stepless) and faster tensioning of the cable 510 resulting in a shorter use time. The mini cable tensioner 600 also provides easier handling which reduces the attention that a user has to give to handling the mini cable tensioner 600. Further, the mini cable tensioner 600 facilitates two handed use which allows a single user to operate the mini cable tensioner 600. The mini cable tensioner 600 protects and covers the cable 510 and only a few components actually enter the patient, specifically, the tensioning tube 800, which will become contaminated. Therefore, the tensioning tube 800 is entirely removable for reprocessing. However, the tensioning grip 700 and the tensioning unit 400 are less likely to be contaminated and therefore can be thoroughly sanitized and used for the next procedure.

The mini cable tensioner 600 provides a ready to use system that does not require any assembly. This allows the user to immediately tension the cable 510 after removal from the packaging. As the mini cable tensioner 600 is pre-assembled, the user may use the system directly after boring a hole and inserting the cable 510.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A tensioning and crimping tool for introducing tension on a cable and crimping a crimp onto the cable, the tensioning and crimping tool comprising:
a housing unit,
a crimping section comprising:
a housing,
a trigger-handle mounted to the housing,
a crimping unit, including an inner crimping tube and an outer crimping tube, where the inner crimping tube is mounted inside the housing having a distal end configured to receive the cable and an outer crimping tube mounted around the inner crimping tube and configured to move in an axial direction relative to the inner crimping tube to crimp a crimp onto the cable when actuated by the trigger-handle,
a tensioning section comprising:
the housing,
a collet opener end at a proximal end of the inner crimping tube, and
a tensioning unit comprising:
a collet axially positioned in a cone sheath,
a tensioning rod having a proximal end connected to an end stop nut and a distal end connected to the cone sheath,
a tensioning nut rotatable on the tensioning rod,
an inner spring configured to actuate the collet in a first direction, and
an outer spring configured to actuate the tensioning rod in a second direction, the second direction being opposite to the first direction.

2. The tensioning and crimping tool of claim 1, further comprising:
the housing unit further comprising:
the housing,
the trigger-handle,
a first bearing bolt,
a knee lever,
a second bearing bolt and
a safety catch connected to the housing over the second bearing bolt configured to prevent the trigger-handle from actuating.

3. The tensioning and crimping tool of claim 2, further comprising:
the housing unit further comprising:
a leaf spring configured to push the trigger-handle relative to the housing.

4. The tensioning and crimping tool of claim 1, wherein the outer crimping tube is configured to move towards the distal end when the trigger-handle is actuated and reaches a mechanical end stop when crimping stop bolts are in contact.

5. The tensioning and crimping tool of claim 1, wherein the cable is configured to pass through the inner crimping tube, the collet, the tensioning rod and the end stop nut.

6. The tensioning and crimping tool of claim 1, wherein the outer crimping tube is configured to move axially relative to the inner crimping tube.

7. The tensioning and crimping tool of claim 1, wherein the collet is configured to radially contract when the inner spring pushes the collet into the cone sheath.

8. The tensioning and crimping tool of claim 1, wherein rotation of the tensioning nut in a clockwise direction towards the distal end increases tension on the cable and rotation of the tensioning nut in a counter clockwise direction towards the proximal end decreases tension on the cable.

9. The tensioning and crimping tool of claim 1, further comprising:
the tensioning unit further comprising:
a guiding cam connected to the cone sheath.

10. The tensioning and crimping tool of claim 1, wherein the end stop nut includes a plurality of fixation slots on a proximal end of the end stop nut.

11. The tensioning and crimping tool of claim 1, wherein tension is configured to be applied to the cable on a first axis along the cable and crimping is configured to be applied to the cable on the first axis.

12. The tensioning and crimping tool of claim 1, wherein the trigger-handle is mounted to the housing over the first bearing bolt, the knee lever and the second bearing bolt.

13. The tensioning and crimping tool of claim 1, wherein tensioning stop slots at a distal end of the tensioning nut and tensioning stop bolts in the housing interact to stop any axial displacement and rotation of the tensioning nut relative to the housing and prevent tensile force greater than 600N.

14. The tensioning and crimping tool of claim 1, wherein tensioning and crimping is uniaxial without radial deflection of the cable.

15. The tensioning and crimping tool of claim 1, wherein the length of the crimping section remains the same which creates constant tension in the cable.

16. The tensioning and crimping tool of claim 1, wherein the crimping unit is configured to be connected with a distal end of the housing unit.

17. The tensioning and crimping tool of claim 1, wherein
the crimping unit is configured to be connected with the housing, where the outer crimping tube is guided on the inner crimping tube and secured axially by a tooth of the trigger-handle, and
the inner crimping tube is connected to the housing over a coupling part at a proximal end of the inner crimping tube.

18. The tensioning and crimping tool of claim 1, wherein the crimping unit consists of an inner crimping tube and an outer crimping tube, where the inner crimping tube is made from a single part and the outer crimping tube is made from a single part.

19. The tensioning and crimping tool of claim 1, wherein the housing unit is configured to be connected with a distal end of the tensioning unit.

20. The tensioning and crimping tool of claim 1, wherein the housing unit is configured to be connected with a proximal end of the crimping unit.

21. The tensioning and crimping tool of claim 1, wherein the tensioning unit is configured to be connected with a proximal end of the housing unit.

* * * * *